United States Patent
Nique

(10) Patent No.: US 6,479,476 B1
(45) Date of Patent: Nov. 12, 2002

(54) 19-NOR STEROIDS SUBSTITUTED IN POSITION 11β, PREPARATION METHOD AND INTERMEDIATES, APPLICATION AS MEDICINES AND PHARMACEUTICAL COMPOSITIONS CONTAINING THEM

(75) Inventor: Francois Nique, Le Perraux sur Marne (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/554,783

(22) PCT Filed: Nov. 16, 1998

(86) PCT No.: PCT/FR98/02437

§ 371 (c)(1),
(2), (4) Date: May 30, 2000

(87) PCT Pub. No.: WO99/25725

PCT Pub. Date: May 27, 1999

(30) Foreign Application Priority Data

Nov. 17, 1997 (FR) .............................................. 97 14357

(51) Int. Cl.$^7$ .............................................. A61K 31/58

(52) U.S. Cl. ........................ 514/176; 514/179; 540/107; 552/626

(58) Field of Search ................................. 552/625, 626, 552/646; 514/176, 179; 540/107

(56) References Cited

U.S. PATENT DOCUMENTS 4,978,657 A * 12/1990 Teutsch et al. .............. 514/175

* cited by examiner

*Primary Examiner*—Barbara P. Badio
(74) *Attorney, Agent, or Firm*—Bierman, Muserlian and Lucas

(57) ABSTRACT

A compound selected from the group consisting of the compounds of the formula

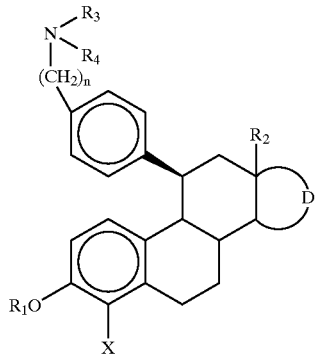

wherein the substituents are defined as in the specification and their addition salts with non-toxic, pharmaceutically acceptable acids and bases having estrogenic activity at the bone level but little or no endometrial hyperplasia activity nor any activity for proliferation of mammary tumors.

9 Claims, No Drawings

19-NOR STEROIDS SUBSTITUTED IN POSITION 11β, PREPARATION METHOD AND INTERMEDIATES, APPLICATION AS MEDICINES AND PHARMACEUTICAL COMPOSITIONS CONTAINING THEM

This application is a 371 of PCT/FR98/02437 filed Nov. 16, 1998.

The present invention concerns 19-nor steroid compounds, substituted in position 11β, their preparation process and intermediates, their application as medicines and the pharmaceutical compositions containing them.

Osteoporosis is a pathology that is characterised by a quantitative and qualitative reduction of the bone tissue, sufficient to lead to vertebral or peripheral fractures, in a spontaneous manner or with minimum traumatism. Although this ailment is of multifactorial origin, it is the menopause that, in women, constitutes the dominating factor of bone loss or osteopenia.

This osteopenia shows itself by rarefaction and modification of the structure of spongy bone which has the consequence of accentuating skeletal fragility and the risk of fracture. The bone loss strongly accentuates after the menopause because of the suppression of ovarian function and reaches 3 to 5% per year to slow down after the age of 65 years.

In a therapeutic objective, postmenopausal hormonal deficiency can be compensated by hormone replacement therapy where oestrogen plays a major role in preserving the bone reserves. But long term oestrogen therapy is sometimes accompanied by undesirable effects on the genital organs (endometrial hyperplasia, mammary tumours), this constitutes a major drawback and limits its application.

It is thus advisable to find other compounds than oestradiol with a dissociated oestrogen activity, namely oestrogen activity at bone level, whilst having little or no endometrial hyperplasia activity, nor the activity of proliferating mammary tumours.

The invention thus has as its object the compounds of general formula (I):

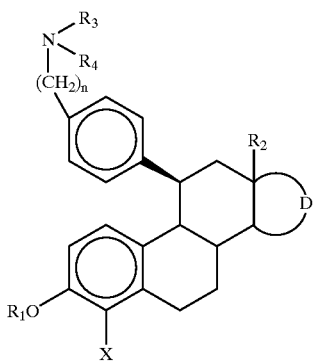

in which:
R$_1$ represents a hydrogen atom, a (CH$_2$)$_m$-Ar, (CO)-Ar, (CH$_2$)$_m$-Alk or (CO)-Alk radical,
R$_2$ represents a radical derived from a saturated or unsaturated, linear or branched hydrocarbide containing from 1 to 6 carbon atoms
D represents the residue of a pentagonal or hexagonal ring optionally substituted and optionally unsaturated,
X represents a halogen or hydrogen atom, n is equal to 3, 4 or 5, either identical or different R$_3$ and R$_4$ representing a hydrogen atom, a (CH$_2$)$_m$-AR, (CH$_2$)$_m$-Het or (CH$_2$)$_m$-Alk group,
or R$_3$ and R$_4$ together with the nitrogen atom to which they are linked form an aromatic or non aromatic, saturated or unsaturated mono or polyclique heterocycle, with 3 to 15 bonds optionally containing from 1 to 3 additional heteroatoms chosen from amongst non substituted or substituted oxygen, sulphur and nitrogen,
Ar representing a carbocyclic aryl group containing from 6 to 18 atoms of carbon, Het representing a saturated or unsaturated aromatic or non aromatic heterocycle, comprising from 1 to 9 carbon atoms and from 1 to 5 heteroatoms chosen from amongst oxygen nitrogen or sulphur atoms, Alk representing a radical derived from a non aromatic, linear, branched or cyclique, saturated or unsaturated hydrocarbide and comprising from 1 to 12 carbon atoms, the Ar radicals Het or Alk can be substituted or non substituted, m represents 0, 1, 2 or 3, as well as their addition salts with the bases or the acids.

By halogen is meant: iodine, bromine, chlorine or fluorine.

By (CH$_2$)$_m$ is meant the following values: single bond in the event that m is equal to 0, CH$_2$, (CH$_2$)$_2$ and (CH$_2$)$_3$.

By the term Ar representing the carbocyclic aryl group containing from 6 to 18 carbon atoms, is meant an aromatic cyclic hydrocarbide derivative such as the phenyl, naphtyl, phenanthrenyl radical or even a condensed bicyclic or tricyclic hydrocarbide derivative comprising a benzene ring like indanyl, indenyl, dihydronaphtyl, tetrahydronaphtyl or fluorenyl. The coupling is made at the benzene ring. It preferably concerns phenyl.

By the term (Het) representing an aromatic or non aromatic, saturated or unsaturated heterocycle, comprising from 1 to 9 carbon atoms and from 1 to 5 heteroatoms chosen from amongst oxygen, nitrogen and sulphur atoms these are notably designated:

Heterocyclic monocyclic radicals, for example thienyl, furyl, pyrannyl, pyrrolyl, imadazoyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazollinyl, triazolyl, tetrazolyl, the heterocyclic condensed rings, for example benzofurannyl, benzothienyl, benzimidazoyl, benzothiazolyl, naphto [2,3-b] thienyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phtalazinyl, naphtyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl radicals or even condensed polycyclic systems, made up of monocyclic heterocyclics like those defined above like for example furo[2,3-b] pyrrol or thieno[2,3-b]furan, or saturated heterocycles such as pyrrolidine, piperidine and morpholine.

By the term (Alk) representing a radical derived from a saturated or unsaturated, branched or cyclic, linear, non aromatic hydrocarbide, are designated, in the case of acyclic hydrocarbides alkyl radicals such as methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethylpentyl, 3-ethylpentyl, n-octyl, 2,2-dimethylhexyl, 3,3- dimethylhexyl, 3-methyl3-ethylpentyl, nonyl, 2,4-dimethylheptyl or n-decyl, radical alkenyls such as vinyl, propenyl, isopropenyl, allyl, 2-methylallyl, butenyl or isobutenyl, or alkynyl radicals such as ethynyl, propynyl, propargyl, butynyl or isobutynyl, and in the case of cyclic radicals, the cycloalkyl radicals, such as cyclopropyl, cyclobutyl, cyclopentyl or cyclohexyl.

Preferably methyl and ethyl radicals are used.

By CO-Alk is preferably meant $COCH_3$ and COEt, by CO-Ar is preferably meant the benzoyl radical, when m is different to zero, $(CH_2)_m$-Ar will preferably be the benzyl group.

When $R_3$ and $R_4$ together with the nitrogen atom to which they are linked form a heterocycle, they are notably mono or bicyclic heterocycles optionally containing another heteroatom chosen from amongst oxygen and nitrogen such as the following unsaturated heterocycles: pyrrolyl, imidazolyl, indolyl, pyridyl, pyrazinyl, pyrimidinyl, pyridazinyl, thiazolyl, oxazoyl, furazolinyl, pyrazolinyl, thiazolinyl, or more particularly, the following saturated heterocycles:

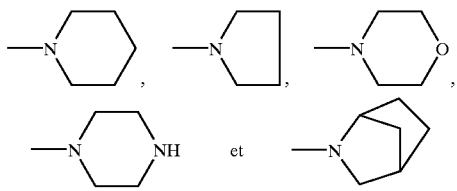

When the different Alk, Ar, Het groups as well as the residue of a pentagonal or hexagonal ring cited earlier are substituted, they could notably be so by the following radicals: halogen, namely fluorine, chlorine, bromine or iodine, alkoxy such as methoxy, ethoxy, propyloxy, isopropyloxy, butyloxy, alkylthio such as methylthio, ethylthio, propylthio, isopropylthio, butylthio, amino, alkylamino such as methylamino or ethylamino, dialkylamino such as dimethylamino, diethylamino, methylethylamino, each of these dialkylamino radicals being optionally in oxidised form, aminoalkyl such as aminoethyl or aminoethyl, dialkylaminoalkyl such as dimethylamino methyl or ethyl, dialkylaminoalkyloxy such as dimethylamino ethyloxy, optionally acylated hydroxyl, acyl such as acetyl, propionyl, butyryl, benzoyl, free carboxy, esterified like alkoxy carbonyl for example methoxy carbonyl or ethoxy carbonyl, cyano, trifluoromethyl, aryl such as phenyl, aralkyl such as benzyl, alkyl, alkenyl or alkynyl these radicals being themselves optionally substituted by the halogen, alkyl, alkoxy, alkylthio, amino, alkylamino or dialkylamino radicals indicated above.

Of course, the expression "substituted" indicates that one or several identical or different substitutes, can be present. As an example, when the alkyl group is a methyl radical substituted by one or several halogen atoms, it can notably be $CH_2Cl$, $CH_2F$, $CHF_2$ and $CF_3$.

In the case of (Het), the substitutes can be at the level of NH or of a carbon atom.

Of course the values of $R_1$, $R_2$, $R_3$, and $R_4$, are independent from each other.

The invention naturally extends to the salts of the compounds of formula (I), like for example the salts formed with mineral or organic acids on the amine. It can thus concern chlorhydric, bromhydric, nitric, sulfuric, phosphoric, acetic, formic, propionic, benzoic, maleic, fumaric, succinic, tartric, citric, oxalic, glyoxylic, aspartic, alcane sulfonic acids such as methane or ethane, sulfonic, arylsulfonic acids, like the sulfonic and arylcarboxylic benzene or paratoluene acids. When the compounds of formula (I) include an acid function, the invention extends to the optionally substituted salts of alkaline, earthy alkaline or ammonium metals.

The invention more particularly has as its object the compounds of general formula (I) as described above, in which (D) represents the residue of a pentagonal ring of formula:

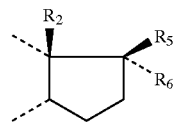

in which $R_2$ retains the same signification as before, either $R_5$ represents an OH, O—$(CH_2)_m$-Alk, O—(CO)-Alk, O—$(CH_2)_m$-Ar, O—(CO)-Ar, O—$(CH_2)_m$-Het, O—(CO)-Het and $R_6$ represents a hydrogen atom, an alkyl, alkenyl or alkynyl radical containing from 1 to 6 substituted or non substituted carbon atoms, m, Alk, Ar and Het as previously described, or $R_5$ and $R_6$ together with the carbon atom which carries them form in one of the following rings:

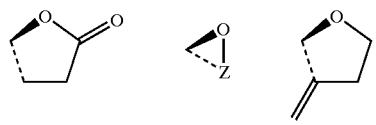

in which z represents a—$(CH_2)_l$—or—CH=CH—$(CH_2)_{l'}$ group, 1 being an integer between 1 and 4 and l'being an integer equal to 1 or 2, either $R_5$ and $R_6$ together form an oxo group, as well as their addition salts with the acids or the bases.

The invention has more particularly as its object the compounds of formula (I) as previously described corresponding to general formula (I'):

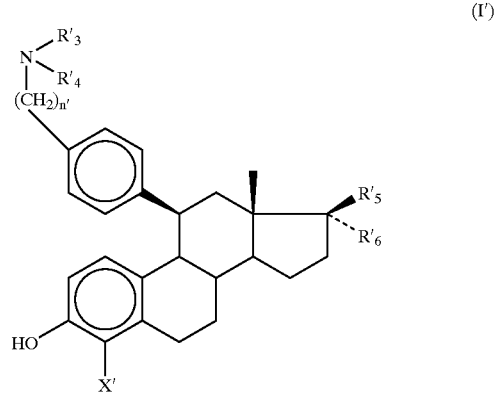

(I')

in which:

X represents a chlorine, bromine or hydrogen atom, n' is equal to 3, or identical or different $R'_3$ and $R'_4$ represent an alkyt radical containing from 1 to 6 carbon atoms or $R'_3$ and $R'_4$ together, with the atom of nitrogen to which they are linked, form a saturated mono or polyclic residue with 3 to 15 bonds optionally containing an additional heteroatom chosen from amongst oxygen, sulphur and nitrogen, R'$_5$ and R'$_6$ have the same signification as R$_5$ and R$_6$, as well as their addition salts with the acids and the bases.

The invention has more particularly as its object the compounds of formula (I) as previously described corresponding to general formula (I') in which:

either R'$_5$ represents an OH radical and R'$_6$ a hydrogen atom, an alkyl, alkenyl or alkynyl radical containing from 1 to 6 substituted or non substituted carbon atoms, or R'$_5$ and R'$_6$ together with the carbon atom which carries them form one of the following rings:

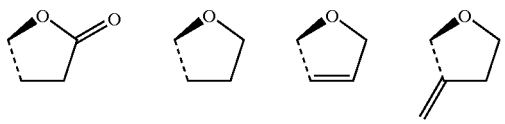

or R'$_5$ and R'$_6$ together form an oxo group, as well as their addition salts with the acids or the bases.

The invention has more particularly as its object the compounds of formula (I) corresponding to general formula (I') as previously described in which:

X' represents a chlorine or hydrogen atom, n' is equal to 3, either identical or different R'$_3$ and R'$_4$ represent an alkyl radical containing from 1 to 6 carbon atoms or R'$_3$ and R'$_4$ together with the nitrogen atom form the following saturated heterocycles:

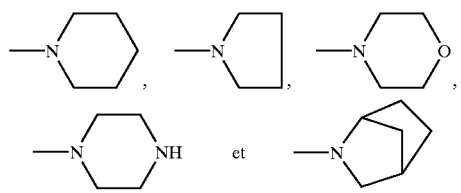

and either R'$_5$ represents an OH radical and R'$_6$ represents a hydrogen atom, an alkyl, alkenyl or alkynyl radical containing from 1 to 6 carbon atoms, substituted or not, or R'$_5$ and R'$_6$ together with the carbon atom which carries them form one of the following rings:

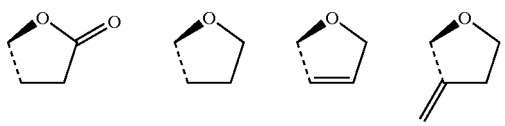

or R'$_5$ and R'$_6$ together form an oxo group, as well as their addition salts with the acids or the bases.

The invention has more particularly as its object either the compounds of general formula (I) as previously described in which X=H, or the compounds of general formula (I) as previously described in which X=Cl or Br, and more particularly Cl.

The invention has very particularly as its object the compounds of formula (I) as well as their addition salts with the acids whose names are the following:

3-hydroxy-11β-[4-[3-(1-piperidinyl)propyl]phenyl]-estra-1,3,5(10)-trien-17-one, 3-hydroxy-11β-[4-[3-(1-pyrrolidinyl)propyl]phenyl]-estra-1,3,5(10)-trien-17-one, 3-hydroxy-11β-[4-[3-dimethylamino)propyl]phenyl]-estra-1,3,5(10)-trien-17-one, 4-chloro-3-hydroxy-11β-[4-[3-(1-piperidinyl)propyl]phenyl]-estra-1,3,5(10) -trien-17-one 4-chloro-3-hydroxy-11β-[4-[3-(1-pyrrolidinyl)propyl]phenyl]-estra-1,3,5(10) -trien-17-one 4-chloro-3-hydroxy-11β-[4-[3-(diethylamino)propyl]phenyl]-estra-1,3,5(10) -trien-17-one 11β-[4-[3-(1-pyrrolidinyl)propyl]phenyl]-estra-1,3,5(10)-trien-3,17β-diol, 11β-[4-(3-dimethylamino)propyl)phenyl]-estra-1,3,5(10)-trien-3,17β-diol 11β-[4-(3-(1-piperidinyl)propyl)phenyl]-estra-1,3,5(10)-trien-3.1 7β-diol 4-chloro-11β-[4-[3-(1-pyrrolidinyl)propyl]phenyl]-estra-1,3,5(10) -trien-3,17β- diol 4-chloro-11β-[4-[3-(1-piperidinyl)propyl(]phenyl]-estra-1,3,5(10) -trien-3,17β-diol 4-chloro-11β-[4-[3-(diethylamino)propyl]phenyl]-estra-1,3,5(10)-trien-3,17β-diol, 17α-methyl-11β-[4-[3-(1-piperidinyl)propyl]phenyl]-estra-1,3,5(10)-trien -3,17β-diol, 4-chloro-17α-methyl-11β-[4-[3-(1-piperidinyl)propyl]phenyl]-estra-1,3,5(10) -trien-3,17β-[diol 11β-[4-[3-(1-piperidinyl)propyl]phenyl]-17α-(trifluoromethyl)-estra-1,3,5(10) -trien-3,17β-diol]

(17R)11β-[4-(3-dimethylamino)propyl)phenyl]-spiro-(estra-1,3,5(10)-trien -17,2'(5'H)-furan)-3-ol (17R)4'.5'-dihydro-11β-[4-(3-dimethylamino)propyl)phenyl]-spiro-(estra -1,3,5(10)-trien-17,2'(3'H)-furan)-3-ol.

The invention equally has as its object a preparation process for the compounds of formula (I) as previously described in which a compound of formula (II) is submitted:

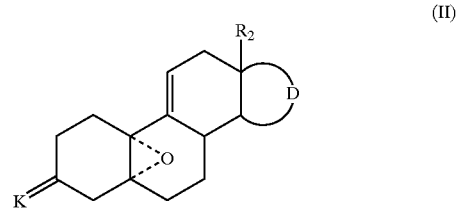

in which

D and R$_2$ are as previously described and K represents a protector group of 3-ceto function, successive to the following reactions:

a) action of a formula (III) compound:

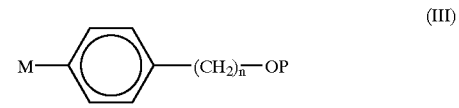

in which, M represents a metallic derivative, P represents an alcohol protector group and n is an integer equal to 3, 4 or 5, then optionally deprotection of one or several protected reagent functions, in order to obtain a formula (III$_a$) compound:

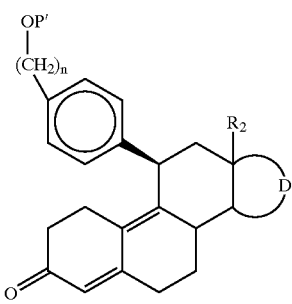

(III$_a$)

P' having the same values as P as well as hydrogen,
b) action, optionally, of a halogenation reagent, in order to obtain a formula (III$_b$) compound:

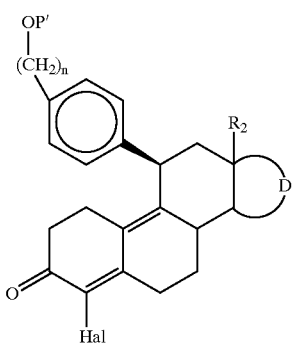

(III$_b$)

Hal representing a halogen atom,
c) after having optionally protected and/or activated the OH function, action of an aromatisation reagent of ring (A) on the formula (III$_a$) and (III$_b$) compounds, then action of a base to obtain the formula (IV) compound:

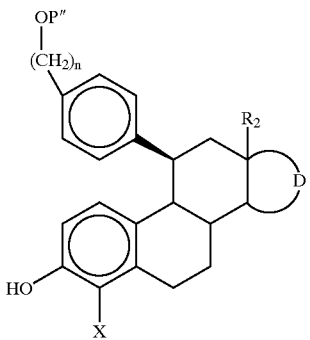

(IV)

P" having the same values as p' and able moreover to represent an activating group,
X being as previously described,
d) action of a formula (V) amine:

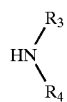

(V)

$R_3$ and $R_4$ being as previously defined, this compound optionally being in the form of a salt, in order to obtain certain compounds of formula (I), the compounds of formulas (III$_a$), (III$_b$), (IV) and (I) being submitted if desired or if necessary, in a suitable order, to one or several of the following reactions:

protection/deprotection of the OH group(s),
alkylation/acylation of the OH group(s),
action of a reduction agent when D represents the residue of a pentagonal ring as previously described and $R_5$ and $R_6$ together form an oxo group,
action of an organometallic or CF$_3$SIMe$_3$ on the compounds of formula (IV) or (I) with D representing the residue of a pentagonal ring as previously described and $R_5$ and $R_6$ together forming an oxo group,
action of a lactonisation agent on the compounds of formula (IV) or (I) with D representing the residue of a pentagonal ring as previously described and $R_5$ and $R_6$ together forming an oxo group,
action of a reduction agent of the double bond, when D represents the residue of a pentagonal ring as previously described and $R_5$ and $R_6$ together with the carbon that carries them, form an O—(CH$_2$)$_{1'}$—CH=CH—,
action of a reduction agent, when D represents the residue of a pentagonal ring as previously described, and $R_6$ is an alkenyl or alkynyl radical containing from 2 to 6 carbon atoms,
salification.

The action of a compound of formula (III) on the compound of formula (II) is preferably carried out in the presence of a copper salt such as copper chloride I.

The action of a halogenation reagent such as N-bromosuccinimide or N-chlorosuccinimide on the compounds of formula (III$_a$) is notably carried out in the presence of a dipolar aprotic solvent such as dimethylformamide.

The reaction of aromatisation followed by the reaction of saponification (basic action) is carried out according to standard methods such as are described in European patent 0097572. Preferably a compound of acetic anyhydride and acetyl bromide is used as aromatisation agent then a base such as soda in methanol as saponification agent.

By activation of the alcohol is meant the introduction notably of a mesylate, tosylate or triflate which makes it possible to facilitate the nucleophile substitution of the amine of formula (V) on the compounds of formula (IV). The formation of the mesylate, tosylate or triflate from compounds of formula (III$_a$) or (III$_b$) with P' representing hydrogen is carried out in the presence of a base such as triethylamine.

The substitution of alcohol with a halogen atom can equally be envisaged.

The protection and deprotection reactions are standard methods known to a specialist. A quite comprehensive review is found in the following work: Protective groups in organic synthesis T. W. Greene, John Wiley & sons (1981).

The protector group P can represent an alkyl radical containing from 1 to 4 carbon atoms, a benzyl group, a tetrahydropyrannyl group, an R$_C$R$_D$R$_E$Si group, in which identical or different R$_C$, R$_D$ and R$_E$, independently from one another each represent an alkyl radical containing from 1 to 4 carbon atoms or a phenyl group. It particularly concerns the Si(Me)$_2$C$_{me3}$ or —Si(PH)$_2$CMe$_3$ or SiMe$_3$ groups.

As an example, the deprotection reactions of the compounds of formula (III$_a$) or (III$_b$), when P' is a tertbutyl-diphenylsilyl group can be carried out by the action of ammonium tetrabutyl fluoride in solution in tetrahydrofuran.

When P' is a tetrahydropyrannyl group, the deprotection is carried out in the presence of an aqueous acid in an alcoholic solvent and preferably by the action of chlorohydric acid in methanol.

The action of a compound of formula $R_3$—NH—$R_4$ on the compounds of formula (IV) is carried out in standard conditions of nucleophile substitutions, notably in the presence of an aprotic solvent such as tetrahydrofuran, OP'' thus preferably represents an O—$SO_2CH_3$, $OSO_2$—PH—pMe, $OSO_2CPh_3$. OP can equally represent halogen (preferably bromine or iodine).

The alkylisation or acylsation reactions of the OH group in position 3 or 17 are carried out by standard methods known to the specialist.

The reduction of 17-ceto in a corresponding alcohol ($R_5$=OH and $R_6$=H) is carried out according to standard methods, notably by the action of an alkaline borohydrure such as sodium borohydrure in methanol or ethanol or by action of aluminium and lithium tetrahydrure.

The action of an organometallic on the 17-ceto makes it possible to have access to the products of formula (I) in which D represents the residue of a pentagonal ring as previously described, $R_5$ is hydroxyl and $R_6$ represents an alkyl, alkenyl, optionally substituted alkynyl radical.

The organometallic derived from an alkyl, alkenyl or alkynyl is chosen from amongst the magnesians of formula AlkMgHal and the lithiens of formula AlkLi in which Alk represents an alkyl, alkenyl or alkynyl group containing at the most 8 carbon atoms and Hal represents a halogen atom. In a preferred method of carrying out the process, Hal represents a chloride, bromine or iodine atom, preferably bromine.

The reaction preferably takes place in the presence of cerium chloride. In a preferred method of carrying out the process Hal represents a chloride, bromine or iodine atom, preferably bromine.

To obtain the compounds of formula (I) with $R_5$ is a hydroxyl and $R_6$ is a $CF_3$ group, the reaction is carried out by action of $CF_3SiMe_3$ on the 17-ceto, followed by the action of a deprotection reagent such as ammonium tetrabutyl fluoride.

The lactonisation reaction starting with 17 ceto is carried out according to the STURTZ method (ref: G STURTZ and J-J. YAOUANC, synthesis, (1980), 289) notably in the presence of allyl bisdimethylamidophosphate in the presence of an alkyllithien such as N-butyllithium in tetrahydrofuran.

The reaction of total or partial reduction when $R_6$ is an alkenyl or alkynyl radical or when $R_5$ and $R_6$ together with the carbon that carries them, form an O—$(CH_2)_1$—CH=CH—group, can be carried out either totally by the action of hydrogen in the presence of a catalyst such as palladium on carbon or a rhodium catalyst such as Wilkinson's reagent or partially (alkynyl becomes alkenyl) by the action of a poisoned catalyst such as palladium on barium sulphate poisoned by pyridine or triethylamine.

The reactions of esterification and salification are carried out by standard methods known to the specialist.

The invention has more particularly as its aim a process for preparing compounds of formula (I') as previously described, in which a compound of general formula (II') is submitted:

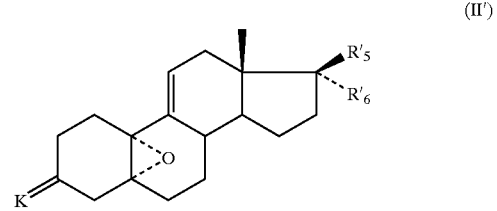

(II')

in which

K, $R'_5$ and $R'_6$ are as previously described, or in which $R'_5$ is a CN radical and $R'_6$ is a protected hydroxyl, successive to the following reactions:

a) action of a compound of formula (III'):

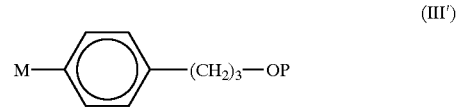

(III')

in which M and P are as previously described, then deprotection of one or several of the protected reactive functions, in order to obtain a compound of formula (III'$_a$):

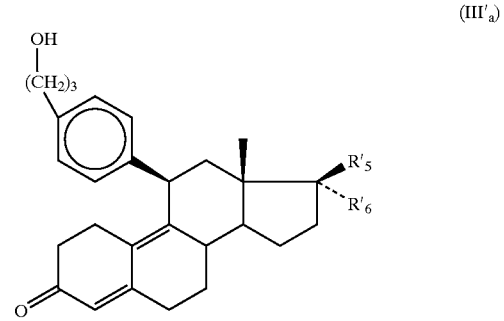

(III'$_a$)

b) action, optionally, of a halogenation reagent in order to obtain a compound of formula (III'$_b$):

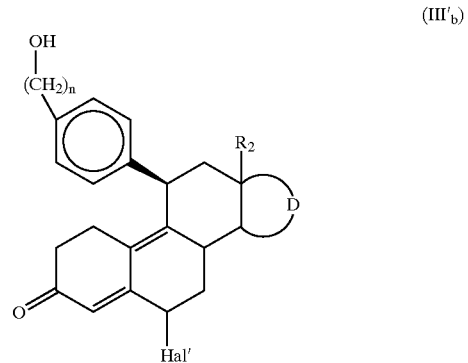

(III'$_b$)

Hal' representing a chlorine or bromine atom, c) activation of the OH function then action of an aromatisation reagent of ring (A) on the compounds of formula (III$_a$) or (III$_b$), then the action of a base to obtain the compounds of formula (IV'):

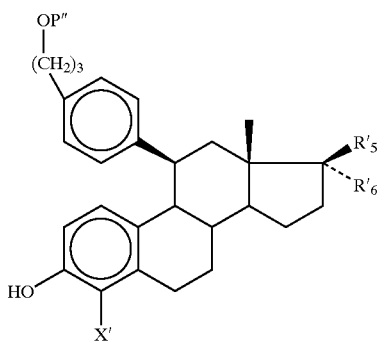

(IV')

X' and P" are as previously described,
d) action of an amine of formula (V'):

(V')

R'₃ and R'₄ as previously described in order to obtain certain components of formula (I'), the compounds of formulas (III'ₐ), (III'ᵦ), (IV') and (I') submitted, if desired or if necessary to one or several of the following reactions:
protection/deprotection of the OH group(s),
alkylation/acylation of the OH group(s),
action of a reduction agent when R'₅ and R'₆ together form an oxo group,
action of an organometallic or CF₃SiMe₃ on the compounds of formula (IV') or (I') with R'₅ and R'₆ together forming an oxo group,
action of a lactonisation agent on the compounds of formula (IV') or (I') with R'₅ and R₆ together forming an oxo group,
action of a reduction agent of the double bond, when R'₅ and R'₆ together with the carbon that carries them, form an O—(CH₂)₁—CH=CH—group,
action of a reduction agent, when R'₆ is an alkenyl or alkynyl radical containing from 2 to 6 carbon atoms,
salification.

The compounds of general formula (I) as well as their addition salts with pharmaceutically acceptable acids notably having oestrogen, anti-oestrogen and antiproliferative activities.

As such, the compounds of formula (I) can be used in the treatment of disorders linked to hypofolliculitis, for example amenorrhea, dysmenorrhea, repeated abortions, premenstrual disorders, in the treatment of certain oestrogen dependent pathologies such as prostatic adenomas or carcinomas, mammary carcinomas and its metastases or the treatment of benign breast tumours, as anti-uterotrophic as well as in the hormone replacement treatment of the menopause or peri-menopause.

Amongst the symptoms and the consequences linked to the menopause, are more precisely meant the hot flushes, sweats, vaginal atrophia and dryness, urinary indications and in the long term lessening of bone mass and the increase of the risk of fracture, as well as the loss of the cardio-vascular protection offered by oestrogens.

In particular, the compounds of formula (I) as well as their addition salts with pharmaceutically acceptable acids or the bases can thus be used in the prevention or the treatment of osteoporosis.

The compounds of formula (I) as well as their addition salts with pharmaceutically acceptable acids or bases, can equally be used in the prevention or treatment of osteoporosis in men.

They can equally be used in the prevention or the (for example cortisone or connected with immobilisation) treatment of secondary osteoporosis.

The compounds of formula (I) as well as their addition salts with pharmaceutically acceptable acids or bases notably have a dissociated oestrogenic activity.

By dissociated oestrogenic activity, is meant oestrogenic activity at bone level whilst only manifesting a minimal activity at uterine level thus leading to the absence of endometrial proliferation (activity well below that of oestradiol).

Furthermore, the compounds according to the invention present the following advantages:

They show an anti-oestrogen and/or antiproliferative activity in the breast. Unlike oestradiol they do not stimulate the growth of human mammary tumour cells and can even inhibit their growth. The compounds according to the invention are thus particularly advantageous for the treatment of the menopause as far as women at risk from mammary cancer are concerned (prior family history) who are thus excluded from replacement oestradiol treatment.

They can equally be used in the treatment of mammary cancers.

They lead to a lowering in the level of serum cholesterol to an at least equivalent level of that induced by oestradiol. They thus reinforce cardiovascular protection.

Finally these compounds according to the invention do not show any oestrogen activity at uterine level, do not need to be administered in association with a progestomimetic compound.

The invention thus has as its object the compounds of formula (I) as well as their addition salts with pharmaceutically acceptable acids or bases, as medicines.

The invention has more particularly as its object the compounds of formula (I) as well as their addition salts with the pharmaceutically acceptable acids or bases, as medicines intended for the prevention or treatment of osteoporosis.

The invention extends to pharmaceutical compositions containing as active ingredient at least one of the medicines as described above.

The compounds of formula (I) are used by digestive, parenteral or local route, for example by percutaneous route. They can be prescribed in the form of simple tablets or sugar coated pills, capsules, granules, suppositories, pessaries, injectable preparations, ointments, creams, gels, microspheres, implants, intravaginal rings, patches, which are prepared according to usual methods.

The active ingredient(s) can be incorporated into excipients usually used in these pharmaceutical compositions, such as talc, gum arabic, lactose, starch, magnesium stearate, cocoa butter, aqueous or non aqueous mediums, fatty bodies of animal or vegetable origin, paraffin derivatives, glycols, various dilution, dispersant or emulsifying agents, preservatives.

The useful dosage varies according to the condition to be treated and the administration route; it can vary for example from 1 to 1000 mg per day in adults by oral route.

The compounds of general formula (II) or (II') are compounds known and described in the European Patent 0057115.

The compounds of formula (III) are known or are easily accessible to the specialist starting with the corresponding aromatic halides. The amines of formula (V) are equally known or easily accessible to a specialist.

The invention equally has as its aim, as intermediary products, the compounds of formula (III$_a$), (III$_b$), (III'$_a$), (III'$_b$), (IV) or (IV').

The examples below illustrate the invention without at the same time limiting it.

Solvents described in the examples: AcOEt (ethyl acetate), TEA (triethylamine), CH$_2$Cl$_2$ (dichloromethane), CHCl$_3$ (chloroform), MeOH (methanol), NH$_4$OH (ammonium hydroxide), iPrOH (isopropyl alcohol).

Preparation 1

11β-[4(3-hydroxypropyl)phenyl]-estra-4,9-diene-3,17-dione

Stage A: Alkylation 3-(4-bromophenyl)-2-propynol

To a solution under inert gas of 55.2 g of 4-bromo iodo benzene at 97% in 230 ml of DMF, 56 ml of TEA is added, 12.2 ml of propargylic alcohol, 1 g of copper iodide and 1.1 g of PdCl$_2$ (PPh$_3$)$_2$ whilst maintaining the temperature at 47° C. After stirring for 3 hours 15 minutes at ambient temperature, it is poured into water, drawn off, washed dried and evaporated under reduced pressure until 48.3 g of raw product is obtained that is purified by chromatography on silica by eluting with the compound CH$_2$Cl$_2$/AcOEt 95/5. 36, 37 g of expected pure product is obtained. (F=80° C.)

Rf (CH$_2$Cl$_2$/AcOEt 95/5): 0.32

IR (CHCl$_3$)

OH 3609cm$^{-1}$

C≡C 2240 cm$^{-1}$

Aromatic 1585 and 1486 cm$^{-1}$

Stage B: Reduction 3-(4-bromophenyl)-propanol

To a solution under inert gas of 36.4 g of 3-(4-bromophenyl)-2-propynol (stage A) in 200 ml of ethanol at 5% of toluene, is added 200 ml of toluene, 7.9 g of Wilkinson's reagent and hydrogen at 1900 mbar for 5 hours. It is evaporated at reduced pressure until the obtainment of 45.9 g of raw product that is purified by chromatography on silica by eluting with the compound CH$_2$Cl$_2$/AcOEt 95/5. 30.1 g of expected product is obtained.

Rf (CH$_2$Cl$_2$/AcOEt 95/5): 0.28

IR (CHCl$_3$)

OH 3626 cm$^{-1}$

Aromatic 1592 and 1489 cm$^{-1}$

Stage C: Protection of the Alcohol (1.1-dimethylethyl)dimethyl[[3-(4-bromophenyl)propyl]oxy]silane To a solution under inert gas of 30.1 g of 3-(4-bromophenyl)-propanol (stage B) in 300 ml of CH$_2$Cl$_2$ is added 11.4 g of imidazol and 23 g of dimethylterbutylsilyl chloride. After stirring for 45 minutes at ambient temperature, it is washed in water, dried and evaporated under reduced pressure until 47.46 g of raw product is obtained that is purified (after having added 1.5 g of an identical trial) by redistillation. 44.8 g of expected pure product is obtained.

Rf (CH$_2$Cl$_2$/AcOEt 95/5): 0.8

IR (CHCl$_3$)

OSi 1527 cm$^{-1}$ and 836 cm$^{-1}$

Aromatic 1590 cm$^{-1}$(f) and 1489 cm$^{-1}$

Stage D: Introduction of the Aryl Group in Position 11 of the Steroid

11β-[4-(3-hydroxypropyl)phenyl]-estra4.9-diene-3,17dione

Preparation of the Magnesian

To 2.67 g of magnesium (shavings) in 5 ml of THF under inert atmosphere and at ambient temperature, is added in 50 minutes at the reflux after priming to 1.2-dibromoethane, a solution of 32.9 g of (1.1-dimethylethyl)dimethyl[[3-(4-bromophenyl)propyl]oxy]silane (stage C) in 100 ml of THF and maintained 5 hours at reflux. (Heading by iodometry: 0.86 M)

Epoxide Opening

To the compound made up of 120 ml of magnesian, obtained at the preceding stage and 600 mg of copper chloride, under inert atmosphere at 0–5□Ca solution of 17.18 g of 5α,10α-epoxy-3.3-[1.2-ethanediylbis(oxy)]-17α-[(trimethylsilyl)oxy]-estr-9(11)-ene-17α-carbonitrile is added (prepared according to the method described in J. C. Gasc and L. Nedelec Tetrahedron Letters (1971), 2005) in 100 m of THF, stirred for 45 minutes at this temperature then poured into a solution of ammonium chloride, drawn off, washed and evaporated under reduced pressure until 43.5 g of raw product is obtained.

Acid Hydrolysis

To a solution of 43.5 g of product obtained from the preceding stage in 300 ml of methanol, under inert atmosphere and at ambient temperature, 60 ml of chlorhydric acid 6 m is added and stirred for 1 hour at ambient temperature. After distillation of the methanol, ethyl acetate is added, it is washed, dried and evaporated under reduced pressure until 30 g of raw product is obtained (F=254° C.).

Cleaving of the Cynhydrine

To a solution of 30 g of product obtained at the preceding stage in 200 ml of methanol, under inert atmosphere and at ambient temperature, 8 ml of washing soda is added and stirred for 1 hour at ambient temperature. After distillation of the methanol, ethyl acetate is added, it is washed, dried and evaporated under reduced pressure until 27.9 g of raw product is obtained that is firstly purified by chromatography by eluting with the compound CH$_2$Cl$_2$/MeOH 95/5. 13 g of expected product (F=192° C., Rf (CH$_2$Cl$_2$/MeOH 95/5): 0.28) is then obtained by dissolving in a compound of 70 ml of CH$_2$Cl$_2$/and 70 ml of isopropylic ether that is concentrated to crystallisation. 11.92 g of pure expected product is obtained.

| F = 192° C. | |
|---|---|
| RMN (CDCl3 300 MHZ) | |
| 0.55(s) | CH$_3$ in 18 |
| ~1.33 | OH |
| ~3.66(m) | C$\underline{H}_2$—OH |
| 4.41(d) | H11 |
| 5.80(s) | H4 |

EXAMPLE1

3-hydroxy-11β-[4-[3-(1-piperidinyl)propyl]phenyl]-estra-1,3,5(10)-trien-17-one

Stage A: Formation of Mesylate

11β-[4-[3-[(methylsulfonyl)oxy]propyl]phenyl]-estra-4.9-diene-3,17-dione

To a solution of 3.41 g of 11β-[4-(3-hydroxypropyl)phenyl]estra-4.9-diene-3,17-dione prepared to preparation 1 in 30 ml of CH$_2$Cl$_2$, under inert atmosphere and at ambient temperature, 1.53 ml of TEA and 0.72 ml of sulfonyl methane chloride in solution in 2 ml of CH$_2$Cl$_2$ is added whilst maintaining the temperature at 0–5° C. and stirring at this temperature. After washing and drying it is evaporated under reduced pressure until 4.15 g of expected raw product is obtained.

| | | |
|---|---|---|
| F = 196° C. | | |
| Rf (CH$_2$Cl$_2$/Acetone 8/2): 0.51 | | |
| RMN (CDCl3) 300 MHZ | | |
| 0.54(s) | | CH$_3$ in 18 |
| 3.00(s) | | OSO$_2$C$\underline{H}_3$ |
| 4.21(t) | J = 5.5 | C$\underline{H}_2$—OSO$_2$ CH$_3$ |
| 4.41(dl) | J = 7 | H11 |
| 5.80(s) | | H4 |
| 7.11 | | H aromatics |

Stage B: Aromatisation of Ring A ps 3-hydroxy-11β-[4-[3-[(methylsulfonyl)oxy]propyl]phenyl]estra-1,3,5(10)-trien-17-one a) Aromatisation To a solution of 4.15 g of dienone prepared in the preceding stage in 40 ml of CH$_2$Cl$_2$, under inert atmosphere and at ambient temperature, whilst cooling in an ice bath, 4 ml of acetic anhydride and 2 ml of acetyl bromide is added and stirred for 1 hour.

b) Saponification

It is evaporated under reduced pressure, 20 ml of THF is added under inert atmosphere and 20 ml of methanol then 28 ml of soda 2N is added whilst cooling in an ice bath. It is stirred for 40 mn, acidified with chlorhydric acid 2N, drawn off with ethyl acetate, washed in salt water then evaporated under reduced pressure until 4.54 g of raw product is obtained that is purified by chromatography by eluting with the CH$_2$Cl$_2$/AcOEt 9/1 compound. 3.18 g of expected product is obtained and 590 mg of a second product (3-ceto-5(10),9(11)-diene).

| | |
|---|---|
| Rf (CH$_2$Cl$_2$/AcOEt 9/1): 0.23 | |
| RMN (CDCl$_3$) 300 MHz | |
| 0.43(s) | CH$_3$ in 18 |
| 2.92(s) | OSO$_2$C$\underline{H}_3$ |
| 4.02(m) | H11 |
| 4.12(m) | C$\underline{H}_2$—OSO$_2$— |
| 4.61(s) | OH in 3 |
| 6.41(dd) | H2 |
| 6.61 | H4 |
| 6.81(d) | H1 |
| 6.89 and 7.01 | H aromatics |

Stage C: Introduction of the Amine 3-hydroxy-11β-[4-[3-(1-piperidinyl)propyl]phenyl]-estra-1,3,5(10)-trien-17-one To a solution of 1.45 g of mesylate prepared in stage B in 15 ml of THF, under inert atmosphere and at ambient temperature, 2.96 ml of piperidine is added, brought to reflux for 3 hrs, returned to ambient temperature, ethyl acetate is added, it is washed with sodium bicarbonate, with salt water then evaporated under reduced pressure until 1.48 g of raw product is obtained that is purified by chromatography by eluting with the compound CH$_2$Cl$_2$/AcOEt/NH$_4$OH 90/10/0.5. 1.2 g of expected product is obtained.

| | |
|---|---|
| Rf(CH$_2$Cl$_2$/ACOEt/NH$_4$OH 90/10/0.5) 0.35 | |
| RMN(CDCl$_3$) 300 MHz | |
| 0.44(s) | CH$_3$ in 18 |
| 1.59 | N—CH$_2$—C$\underline{H}_2$ of the ring |
| 2.41 | N—C$\underline{H}_2$—CH$_2$ of the ring |
| 4.02(tl) | H11 |
| 6.31(dd) | H2 |
| 6.52(d) | H4 |
| 6.77(d) | H1 |
| ~6.81 and ~6.98 | H aromatics |

EXAMPLE 2

3-hydroxy-11β-[4-[3-(1-pyrrolidinyl)propyl]phenyl]estra-1,3,5(10)-trien-17-one

It is carried out as in example 1 stage C from 456 mg of the mesylate prepared in stage B of example 1 and 0.79 ml of pyrrolidine. 441 mg of raw product is obtained that is purified by chromatography by eluting with the AcOEt/TEA 7/3 compound then by crystallisation in isopropylic ether. 347 mg of expected product is obtained.

| | |
|---|---|
| F = 180° C. | |
| Rf(CH$_2$Cl$_2$/AcOEt/NH$_4$OH 9/1/0.5): 0.33 | |
| RMN(CDCl$_3$) 300 MHz | |
| 0.44(s) | CH$_3$ in 18 |
| 1.75 | N—CH$_2$—C$\underline{H}_2$ of the ring |
| 2.50 | N—C$\underline{H}_2$—CH$_2$ of the ring |
| 4.03(tl) | H11 |
| 6.25(dd) | H2 |
| 6.51(d) | H4 |
| 6.75(d) | H1 |
| ~6.84 and ~6.99 | H aromatics |

EXAMPLE 3

3-hydroxy-11β-[4-[3-dimethylamino)propyl]phenyl]-estra-1,3,5(10)-trien-17-one

It is carried out as in example 1 but using dimethylamine as amine.

EXAMPLE 4

4-chloro-3-hydroxy-11β-[4-[3-(piperidinyl)propyl]phenyl]-estra-1,3,5(10)-trien-17-one Stage A: Chlorination 4-chloro-11β-[4-(3-hydroxypropyl)phenyl]estra-4.9-diene-3-one To a solution of 11.9 g of 11β-[4-(3-hydroxypropyl)phenyl]-estra-4.9-diene-3,17-dione prepared to preparation 1 in 100 ml of DMF, under inert atmosphere and at 60° C., 4.93 g of N-chloro succinimide is added and stirred for 10 mn at this temperature. It is poured into water, drawn off, washed, dried, evaporated under reduced pressure until 16.2 g of raw expected product is obtained that is purified by chromatography by eluting with the compound CH$_2$Cl$_2$/Acetone 85/15. 9.34 g of pure expected product is obtained.

| | |
|---|---|
| Rf(CH$_2$Cl$_2$/Acetone 85/15 | |
| RMN CDCl$_3$) 300 MHZ | |
| 0.56(s) | CH$_3$ in 18 |
| 3.24(dt) | H equatorial |
| 3.65(t) | C$\underline{H}_2$—OH |
| 4.42(d) | H11 |
| ~7.09 | H aromatics |

Stage B: Formation of Mesylate
4-chloro-11β-[4-[3-[(methylsulfonyl)oxy]propyl]phenyl]-estra-4.9-diene-3-one To a solution of 9.34 g of alcohol prepared in stage A in 90 ml of $CH_2Cl_2$, under inert atmosphere and at ambient temperature, 3.86 ml of TEA and 1.82 ml of sulfonyl methane chloride in solution in 5 ml of $CH_2Cl_2$ is added whilst maintaining the temperature at 0–5° C. and stirring for 30 mn at this temperature. After washing and drying it is evaporated under reduced pressure until 11 g of expected raw product is produced.

| Rf($CH_2Cl_2$/Acetone 85/15): 0.3 RMN($CDCl_3$) 250 MHz | |
|---|---|
| 0.56(s) | $CH_3$ in 18 |
| 3.00(s) | $OSO_2CH_3$ |
| 3.26(dt) | H equatorial |
| 4.22(t) | $C\underline{H}_2$—$OSO_2CH_3$ |
| 4.42(dl) | H11 |
| ~7.10 | H aromatics |

Stage C: Aromatisation of Ring A
4-chloro-3-hydroxy-11β-[4-[3-[(methanesulfonyl)oxy]propyl]-phenyl-estra -1,3,5(10)-trien-17-one a) Aromatisation To a solution of 10.37 g of dienone prepared in the preceding stage in 100 ml of $CH_2Cl_2$, under inert atmosphere and at ambient temperature, whilst cooling in an ice bath, 10 ml of acetic anhydride and 2 ml of acetyl bromide, is added and stirred for 6 hours at ambient temperature.

b) Saponification

It is evaporated under reduced pressure, 50 ml of THF is added, 50 ml of methanol then 70 ml of Soda 2N is added whilst cooling in an ice bath. It is stirred for 45 mn, acidified with 70 ml of chlorohydric acid 2N, drawn off in ethyl acetate, washed in salt water then evaporated under reduced pressure until 11.5 g of raw product is obtained that is purified by chromatography by eluting with the cyclohexane/AcOEt 9/1 compound. 6 g of expected product is obtained (Rf=0.27) and 768 mg of a second product (4-chloro-1,3,5(10), 9(11) tetraenone derivative not containing hydroxy in 3 (Rf=0.39)).

| Rf($CH_2Cl_2$/AcOEt 9/1): 0.27 RMN($CDCl_3$) 250 MHZ | |
|---|---|
| 0.43(s) | $CH_3$ in 18 |
| 2.93(s) | $OSO_2C\underline{H}_3$ |
| 4.02(m) | H11 |
| 4.14 | $C\underline{H}_2$—$OSO_2$ |
| 5.46(s) | OH in 3 |
| 6.64 | H2 |
| 6.81 | H1 |
| 6.92 | H aromatics |

Stage D: Introduction of the Amine
4-chloro-3-hydroxy-11β-[4-[3-(1-piperidinyl)propyl]phenyl]-estra-1,3,5(10) -trien-17-one To a solution of 1.5 g of mesylate prepared in the preceding stage in 15 ml of THF, under inert atmosphere and at ambient temperature, 2.96 ml of piperidine is added, brought to reflux for 3 hrs, brought back to ambient temperature, ethyl acetate is added, it is washed with sodium bicarbonate, with salt water then evaporated under reduced pressure until 1.66 g of raw product is obtained that is purified by chromatography by eluting with the compound $CH_2Cl_2$/MeOH/$NH_4$OH90/10/0.5. 1.2 g of expected product is obtained.

| Rf($CH_2Cl_2$/AcOEt/$NH_4$OH 90/10/0O.5): 0.27 RMN($CDCl_3$) 300 MHZ | |
|---|---|
| 0.43(s) | $CH_3$ in 18 |
| 1.62 | N—$CH_2$—$C\underline{H}_2$ of the ring |
| 2.46 | N—$C\underline{H}_2$—$CH_2$ of the ring |
| 4.01(tl) | H11 |
| 6.61(d) | H2 |
| 6.79(d) | H1 |
| ~6.89 | H aromatics |

EXAMPLE 5

4-chloro-3-hydroxy-11β-[4-[3-(1-pyrrolidinyl)propyl]phenyl]-estra -1,3,5(10)-trien-17-one It is carried out as in example 4 stage D but from 517 mg of mesylate (example 4 stage C) and 0.84 ml of pyrrolidine.

510 mg of raw product is obtained that is purified by chromatography by eluting with the compound $CH_2Cl_2$/MeOH/$NH_4$OH 90/10/1. 380 mg of expected product is obtained.

| Rf($CH_2Cl_2$/AcOEt/$NH_4$OH 90/10/1): 0.3 RMN($CDCl_3$) 300 MHz | |
|---|---|
| 0.42(s) | $CH_3$ in 18 |
| 1.75 | N—$CH_2$—$C\underline{H}_2$ of the ring |
| 2.46 | N—$C\underline{H}_2$—$CH_2$ of the ring |
| 4.02(sl) | H11 |
| 6.56(d) | H2 |
| 6.79(d) | H1 |
| 6.89(AA'BB') | H aromatic |

EXAMPLE 6

4-chloro-3-hydroxy-11β-[4-[3-(diethylamino)propyl]phenyl]-estra -1,3,5(10)-trien-17-one It is carried out as in example 4 stage D but from 517 mg of mesylate (example 4 stage C) and 1 ml of diethylamine.

500 mg of raw product is obtained that is purified by chromatography by eluting with the compound $CH_2Cl_2$/MeOH/$NH_4$OH 90/10/1. 385 mg of expected product is obtained.

| Rf($CH_2Cl_2$/AcOEt/$NH_4$OH 90/10/1): 0.31 RMN ($CDCl3$) 3OOMHz | |
|---|---|
| 0.42(s) | $CH_3$ in 18 |
| 0.95 | N—$CH_2$—$C\underline{H}_3$ |
| 2.49 | N—$C\underline{H}_2$—$CH_3$ |
| 4.02(t) | H11 |
| 6.59(d) | H2 |
| 6.80(d) | H1 |
| 6.90(AA'BB') | H aromatics |

EXAMPLE 7

11β-[4-[3-(1-pyrrolidinyl)propyl]phenyl]-estra-1,3,5(10)-trien -3,17β-diol

To a solution of 310 mg of the product obtained in example 2 in 3 ml of methanol, 54 mg of sodium borohydrure at 97% is added at 0–5° C., stirred for 1 hour at this temperature, salt water is added, it is drawn off, washed, dried and evaporated under reduced pressure until 320 mg of raw product is obtained that is purified by chromatography by eluting with the compound CH$_2$Cl$_2$/MeOH/NH$_4$OH 90/10/1. 217 mg of pure expected product is obtained.

| | |
|---|---|
| Rf (CH$_2$Cl$_2$/MeOH/NH$_4$OH): 0.23 | |
| RMN (CDCl$_3$) 300 MHz | |
| 0.33(s) | CH$_3$ in 18 |
| 1.76 | N—CH$_2$—CH$_2$ of the ring |
| 2.52 | N—CH$_2$—CH$_2$ of the ring |
| 3.69(dd) | H17 |
| 3.96(tl) | H11 |
| 6.27(dd) | H2 |
| 6.47(d) | H4 |
| 6.76(d) | H1 |
| ~6.83 and ~6.98 | H aromatics |

EXAMPLE 8

11β-[4-(3-diethylamino)propyl]phenyl]-estra-1,3,5(10)-trien -3,17β-diol

It is carried out as in example 7 (reduction with sodium borohydrure) but from the product obtained in example 3.

| | |
|---|---|
| Rf AcOEt/iPrOH/NH$_4$OH 70/30/1: 0.17 | |
| RMN (CDCl$_3$ + 1 drop of C$_5$D$_5$N) 300 MHz | |
| 0.32(s) | CH$_3$ in 18 |
| 2.18(s) | N—CH$_3$ |
| 3.67 | H17 |
| 3.95 | H11 |
| 6.46(dd) | H2 |
| 6.64(d) | H4 |
| 6.81(d) | H1 |
| ~6.88~7.00 | H aromatics |

EXAMPLE 9

11β-[4-(1-piperidynyl)propyl]phenyl]-estra-1,3,5(10)-trien-3,17β-diol

It is carried out as in example 7 (reduction with sodium borohydrure) but from the product obtained in example 1.

| | |
|---|---|
| Rf ethyl acetate/TEA 90/10: 0.30 | |
| RMN (CDCl$_3$) 300 MHz | |
| 0.33(s) | CH$_3$ in 18 |
| 2.1 to 2.5 | N—CH$_2$, Ph—CH$_2$ |
| 3.70(dd) | H17 |
| 3.96(tl) | H11 |
| 6.32(dd) | H2 |
| 6.47(d) | H4 |
| 6.78(d) | H1 |
| ~6.82~6.98 | H aromatics |

EXAMPLE 10

4-chloro-11β-[4-[3-(1-pyrrolidinyl)propyl]phenyl]-estra -1,3,5(10)-trien-3,17β-diol It is carried out as in example 7 but from 257 mg of product obtained in example 5 and 42 mg of sodium borohydrure at 97%. 221 mg of raw product is obtained that is purified by crystallisation to obtain 154 mg of pure expected product.

| | |
|---|---|
| Rf (CH$_2$Cl$_2$/MeOH/NH$_4$OH 90/10/1): 0.15 | |
| RMN (CDCl$_3$) 300 MHz | |
| 0.33(s) | CH$_3$ in 18 |
| 1.73(m) | N—CH$_2$—CH$_2$ of the ring |
| ~2.37; ~2.50 | N—CH$_2$ and PH—CH$_2$ of the chain |
| 2.43(m) | N—CH$_2$—CH$_2$ of the ring |
| 3.71(dd) | H17 |
| 3.93(tl) | H11 |
| 6.58(d) | H2 |
| 6.76(d) | H1 |
| 6.91 | H aromatics |

EXAMPLE 11

4-chloro-11β-[4-[3-(1-piperidinyl)propyl]phenyl]-estra-1,3,5(10) -trien-3,17β-diol It is carried out as in example 7 but from 305 mg of product obtained in example 4 and 48 mg of sodium borohydrure at 97%. 275 mg of raw product is obtained that is purified by crystallisation in acetone to obtain 170 mg of pure expected product.

| | |
|---|---|
| F = 128° C. | |
| Rf (CH$_2$/Cl$_2$MeOH/NH$_4$OH 90/10/1): 0.25 | |
| RMN (CDCl$_3$) 300 MHz | |
| 0.30(s) | CH$_3$ in 18 |
| 1.55(m) | N—CH$_2$—CH$_2$ of the ring |
| 2.23; 2.41 | N—CH$_2$ and Ph—CH$_2$ of the chain |
| 2.36(m) | N—CH$_2$—CH$_2$ of the ring |
| 3.68(dd) | H17 |
| 3.95(t) | H11 |
| 6.58(d) | H2 |
| 6.79(d) | H1 |
| 6.88 | H aromatics |

EXAMPLE 12

4-chloro-11β-[4-[3-(1-diethylamino)propyl]phenyl]-estra -1,3,5(10)-trien-3,17β-diol It is carried out as in example 7 but from 262 mg of product obtained in example 5 and 42 mg of sodium borohydrure at 97%. 231 mg of raw product is obtained that is purified by chromatography to obtain 223 mg of pure expected product.

| | |
|---|---|
| Rf (CH$_2$Cl$_2$/MeOH/NH$_4$OH 90/10/1): 0.18 | |
| RMN (CDCl$_3$) 300 MHz | |
| 0.30(S) | CH$_3$ in 18 |
| 0.95(t) | N—CH$_2$—CH$_3$ |
| 2.49(q) | N—CH$_2$—CH$_3$ |
| 3.69(t) | H17 |
| 3.95(t) | H11 |
| 6.57(d) | H2 |
| 6.78(d) | H1 |
| 6.91 | H aromatics |

EXAMPLE 13

17α-methyl-11β-[4-[3-(1-piperidininyl)propyl]phenyl]-estra -1,3,5(10)-trien-3,17β-diol 1.2 g of finely ground cerium chloride heptahydrate (CeCl3, 7H2O), is heated for 2 hours under reduced pressure, brought to ambient temperature under inert gas, 12 ml of THF is added, it is stirred for 2 hours at ambient temperature then 1.9 ml of an etherised solution of methyllithium is added at −68° C. After having stirred for 30 mn at −72°C. 300 mg of the product of example 1 in solution in 3 ml of THF is added. The temperature is left to rise to room temperature, then the solution is filtered, washed, dried and evaporated under reduced pressure to obtain 325 mg of raw product that is purified by chromatography by eluting with the compound $CH_2Cl_2/MeOH/NH_4OH$ 90/10/0.5.

| Rf ($CH_2Cl_2$/MeOH/$NH_4OH$ 90/10/0.5): 0.25 RMN ($CDCl_3$) 300 MHz | |
|---|---|
| 0.45(s) | $CH_3$ in 18 |
| 1.29 | $CH_3$ in 17 |
| 4.00(tl) | H11 |
| 6.35(dd) | H2 |
| 6.49(d) | H4 |
| 6.79(d) | H1 |
| ~6.81 and ~6.98 | H aromatics |

EXAMPLE 14

4-chloro-17α-methyl-11β-[4-[3-(1-piperidininyl) propyl]phenyl]-estra-1,3,5(10)-trien-11β-diol It is carried out as in example 13 but from 300 mg of the product prepared in example 4 and 12 ml of an etherised solution of methyllithium. 312 mg of raw product is obtained that is purified by chromatography by eluting with the compound $CH_2Cl_2/MeOH/NH_4OH$ 90/10/1 to obtain 275 mg of pure expected product

| Rf ($CH_2Cl_2$/MeOH/$NH_4OH$ 90/10/1): 0.25 RMN ($CDCl_3$) 300 MHz | |
|---|---|
| 0.45(s) | $CH_3$ in 18 |
| 1.29(s) | $CH_3$ in 17 |
| 1.56(m) | N—$CH_2$—$CH_2$ (ring) |
| 2.34(m) | N—$CH_2$—$CH_2$ (ring) |
| 2.26(m) and 2.46(t) | $CH_2$—N and $CH_2$—Ph (chain) |
| 3.99(tl) | H11 |
| 6.59(d, J = 8, 5 Hz) | H2 |
| 68(d) | H1 |
| ~6.87 | H aromatics |

EXAMPLE 15

11β-[4-[3-(1-piperidininyl)propyl]phenyl]-17α-(trifluoromethyl) -estra-1,3,5(10)-trien-3,17β-diol 1) Preparation of the 17β-trimethylsilyloxy, 17β-trifluormethyl 83 mg of tetrahydrated tetramethylammonium fluoride is dried for 2 hours at 120° C., brought to ambient temperature under inert gas and 236 mg of the product of example 1, 3 ml of THF, and 0.3 ml of trimethyl (trifluoromethyl) silane ($CF_3SiMe_3$) is added whilst maintaining the temperature at 0–5° C. The temperature is left to rise to 10° C. and it is stirred for 2 hours 30 at 0–5° C., then it is poured into salt water, drawn off, washed, dried and evaporated under reduced pressure to obtain 340 mg of raw product.

2) Deprotection of the Alcohol

To a solution of 340 mg of previously obtained raw product in 4 ml of THF, under inert atmosphere and at room temperature, 2 ml of terabutylammonium fluoride in solution 1 M in the THF is added, stirred for 2 hours at room temperature, poured into water, drawn off, washed, dried and evaporated under reduced pressure until 530 mg of raw product is obtained that is purified by chromatography by eluting with the compound $CH_2Cl_2/MeOH/NH_4OH$ 90/10/1 then with the compound AcOEt/TEA 95/5. 96 mg of pure expected product is obtained.

| Rf (AcOEt/TEA 95/5): 0.25 RMN ($CDCl_3$) 300 MHz | |
|---|---|
| 0.50(s) | $CH_3$ in 18 |
| 4.03(tl) | H11 |
| 6.36(dd) | H2 |
| 6.52(dd) | H4 |
| 6.78(d) | H1 |
| ~6.85 and ~6.96 | H aromatics |

EXAMPLE 16

(17R)11β-[4-[3-(dimethylamino)propyl)phenyl]-spiro-(estra -1,3,5(10)-trien-17,2'(5'H)-furan)-3-ol It is carried out as in example 1 but from dimethylamine and 11β-[4-[3-hydroxypropyl)phenyl]-spiro-estra-4.9-diene-17,2'(5'H)-furan)-3-one.

EXAMPLE 17

(17R)4',5'dihydro-11β-[4-[3-(dimethylamino)propyl) phenyl]-spiro-(estra-1,3,5(10)-trien-17,2'(3'H)-furan)-3-ol The reduction is carried out by hydrogenation of the product of example 16 with palladium at 10% on carbon.

| Rf (AcOEt/TEA 8/2): 0.25 RMN ($CDCl_3$) 300 MHz | |
|---|---|
| 0.46(s) | $CH_3$ in 18 |
| 2.20(s) | N—$CH_3$ |
| 3.76(m) | H'3 |
| 3.98(m) | H11 |
| 6.32(dd) | H2 |
| 6.47(d) | H4 |
| 6.78(d) | H1 |
| ~6.83~6.97 | H aromatics |

Pharmacological Tests
1—Effect on the Proliferation of Mammary Cells

The proliferative activity of the molecules is studied comparatively with that of oestradiol on the human mammary cells MCF-7 in culture.

To highlight the agonist effect of oestradiol and/or the molecules tested, the culture medium for the maintenance of the cells (rich in growth factors and in steroids) is replaced by a more impoverished medium, amongst others lacking in steroids (DMEM supplemented by 5% of serum with steroid removed and without phenol red). The cells undergo this deprivation two days before the start of the trial.

After 7 days of culture in the presence of the products to be studied, the cellular proliferation is evaluated by quantitive analysis of the DNA. In each trial, the effect of oestradiol at $10^{-10}$M (cellular growth in the presence of oestradiol less cellular growth in the presence of solvent) determines the agonist activity at 100%. The activity of the molecules is evaluated in comparison to this internal control. The molecules inducing a cellular growth identical to that observed with the solvent alone are classed "inactivated", those inducing cellular growth lower than that observed with the solvent are classed "inhibitor".

|  | ACTIVITY |
| --- | --- |
| Oestradiol | Agonist |
| Example 12 | Inhibitor |
| Example 7 | Inhibitor |
| Example 9 | Inhibitor |
| Example 13 | Inhibitor |
| Example 11 | Mixed |

*Mixed: slight agonist activity in very weak concentrations and inhibitory activity in stronger concentrations.

Conclusion

The products tested are not agonist of the growth of MCF-7 cells, certain ones are even inhibitors of these.

2—Affinity of the Human Oestrogen Receptor (REH)

A cytosolic extract of SF9 cells containing the recombinant human oestrogen receptor is obtained by overexpression in an insect-Baculo-viros system of cells, according to the general methodology described by N. R. WEBB et al. (Journal of Methods in cell and Molecular Biology, (1990) vol 2 n°4, 173–188) and whose application is described for the expression of human hormonal receptors, for example the human glucocorticoid receptor (G.SRINIVASAN et al. Molecular Endocrinology (1990) vol 4 n°2 209–216).

The BaculoGold Transfection Kit (PharMingen, reference 21000K) is used to generate the recombinant baculovirus containing the fragment of DNAc described in the expression vector HEGO by L. TORA et al. (The EMBO Journal (1989) vol 8 n°7 1981–1986) comprising the coding region for the human oestrogen receptor of wild type with glycine in position 400.

The recombinant virus obtained in this way is used to express the progestogen receptor in the cells of insects SF9 (ATCC CRL1711), according to the known methodology previously cited.

$2 \times 10^7$ SF9 cells are cultivated in a 175 cm² "Falcon" flask in TNM-FH "SIGMA" medium supplemented with 10% of foetal calf serum (FCS) and 50 micrograms/ml of gentamycine. After infection then incubation at 27° C. for 40 to 42 hours, the cells are lysed in 1 ml of lyse buffer (Tris 20 mM-HCl pH8, EDTA 0.5 mM, DTT 2mM, Glycerol 20%, KCl 400 mM) by a freezing-defrosting cycle that is repeated twice more. The supernatant, containing the recombinant human oestrogen receptor is preserved in liquid nitrogen in 0.5 ml amounts.

The supernatant is incubated at 0° C. for 24 hours with a consistent concentration (T) of oestradiol tritiated in the presence of growing concentrations either of cold oestradiol $(0–1000 \times 10^{-9}M)$, or of cold product to be tested $(0–25000 \times 10^{-9}M)$. The concentration of linked triated oestradiol (B) is then measured in each incubation by the dextran carbon adsorption technique.

3—Calculation of the Affinity Relative to Linking (ARL)

The 2 following curves are plotted: the percentage of 100×B/BO linked tritiated hormone in comparison to the logarithm of the concentration of cold reference hormone or in comparison to the logarithm of the concentration of cold product tested.

The soundness of the following equation is determined:

$$I_{50}=100(B_0/B_0+Bmin/B_0)/2=100(1+Bmin/B0)=50(1+Bmin/B_0)$$

$B_0$=Concentration of the linked tritiated hormone in the absence of any cold product, B=Concentration of the linked tritiated hormone in the presence of an X concentration of cold product, Bmin=Concentration of linked tritiated hormone for an incubation of this tritiated hormone in concentration (T) in the presence of a large excess of cold reference hormone $(1000 \times 10^{-9})$ for human receptor.

The intersections of the right angle I50 and the curves, make it possible to evaluate the concentration of cold reference hormone (CH) and the tested cold product (CX) which inhibit 50% of the bond of the tritiated hormone on the receptor.

The relative affinity of the link (ARL) of the tested product is determined by the equation:

$$ARL=100(CH)/(CX)$$

The obtained results are the following:

| EXAMPLES | EH oestradiol = 100 24 H |
| --- | --- |
| 12 | 28 |
| 7 | 59 |
| 9 | 28 |
| 13 | 42 |
| 11 | 14 |

Conclusion

The tested products present good affinities for the human oestrogen receptor.

What is claimed is:

1. A compound selected from the group consisting of a compound of the formula

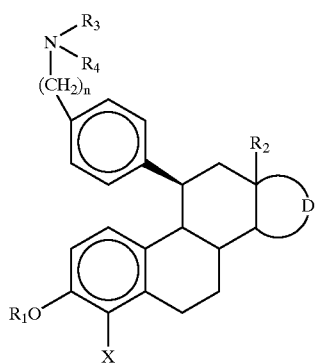

wherein $R_1$ is selected from the group consisting of hydrogen, —$(CH_2)_m$-Ar, —CO-Ar, —$(CH_2)_m$-Alk and —COAlk, m is an integer from 1 to 3, Ar is a substituted or unsubstituted carbocyclic aryl of 6 to 18 carbon atoms, Alk is non-aromatic, substituted or unsubstituted alkyl and cycloalkyl of up to 12 carbon atoms, $R_2$ is an unsaturated or saturated hydrocarbon of up to 6 carbon atoms, D forms a saturated or unsaturated, unsubstituted or substituted pentagonal or hexagonal ring, X is halogen, n is an integer from 3 to 5, $R_3$ and $R_4$ are individually selected from the group consisting of hydrogen, —$(CH_2)_m$-Ar, —$(CH_2)_m$-Het and —$(CH_2)_m$-Alk or taken together form a non aromatic or aromatic, unsaturated or saturated, mono- or polycyclic heterocycle of 3 to 15 ring members and optionally containing 1 to 3 additional heteroatoms selected from the group consisting of oxygen, nitrogen and sulfur, Het is aromatic or non-aromatic, unsubstituted or substituted, unsaturated or saturated heterocyclic of 1 to 9 carbon atoms and 1 to 5 heteroatoms selected from the group consisting of oxygen, sulfur and nitrogen, the substituents for Alk, Ar, Het and D being at least one member of the group consisting of hydrogen, halogen, alkoxy, alklthio, —NH$_2$, alkylamino, dialkylaminoalkyl, dialkylaminoalkoxy, —OH, acyloxy of an organic carboxylic acid of 1 to 6 carbon atoms, —COOH, salified —COOH, —COOAlk, —CN, —CF$_3$, aryl, arylalkyl, alkyl, alkenyl and alkynyl, and D may also be substituted with —O—(CH$_2$)$_m$-Ar, —O—(CO)Ar, —O—(CH$_2$)$_m$-Het, and —O—(CO)-Het and its addition salts with non-toxic pharmaceutically acceptable acids and bases.

2. A compound of claim 1 wherein D is a pentagonal ring of the formula

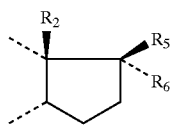

wherein R$_2$, m, Alk, Ar and Het are defined as in claim 1, R$_5$ is selected from the group consisting of —OH, —O—(CH$_2$)$_m$-Alk and —O—(CO)-Alk, R$_6$ is selected from the group consisting of hydrogen and alkyl, alkenyl and alkynyl of up to 6 carbon atoms.

3. A compound of claim 1 having the formula

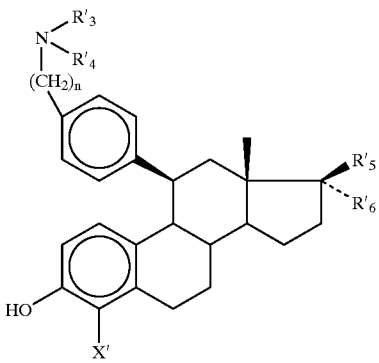

I' wherein X$^1$ is chloring or bromine, n$^1$ is 3, R$^1_3$ and R$^1_4$ are individually alkyl of 1 to 6 carbon atoms or together with the nitrogen form a saturated mono- or polycyclic heterocycle of 3 to 15 ring members and optionally containing an additional heteroatom selected from the group consisting of oxygen, sulfur and nitrogen and R$^1_5$ is selected from the group consisting of —OH, —O—(CH$_2$)$_m$-Alk, —O—(CO)-Alk, —O—(CH$_2$)$_m$-Ar, —O—(CO)Ar, —O—(CH$_2$)$_m$-Het, and —O—(CO) and R$^1_6$ is selected from the group consisting of hydrogen and alkyl, alkenyl and alkynyl of up to 6 carbon atoms.

4. A compound of claim 3 wherein R$^1_5$ is —OH and R$^1_6$ is selected from the group consisting of hydrogen and substituted or unsubstituted alkyl, lakenyl and alkynyl of up to 6 carbon atoms.

5. A compound of claim 3 wherein X' is chlorine, R$^1_3$ and R$^1_4$ are individually alkyl of 1 to 6 carbon atoms or together with the nitrogen form a member of the group consisting of

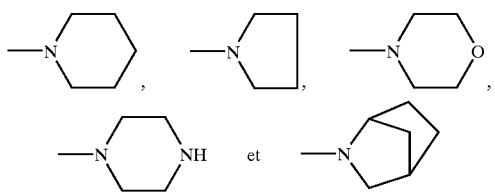

R$^1_5$ is —OH and R$^1_6$ is selected from the group consisting of hydrogen and unsubstituted or substituted alkyl, alkenyl and alkynyl of up to 6 carbon atoms.

6. A compound of claim 1 selected from the group consisting of 4-chloro-3-hydroxy-11β-[4-[3-(1-piperidinyl)propyl] phenyl]-estra-1,3,5(10)-trien-17-one 4-chloro-3-hydroxy-11β-[4-[3-(1-pyrrolidinyl)propyl] phenyl-estra-1,3,5(10)-trien-17-one 4-chloro-3-hydroxy-11β-[4-[3-(diethylamino)propyl] phenyl]-estra-1,3,5(10)-trien-17-one 4-chloro-11β-[4-[3-(1-pyrrolidinyl)propyl]phenyl]-estra-1,3,5(10)-trien-3,17β-diol 4-chloro-11β-[4-[3(piperidinyl)propyl]phenyl]-estra-1,3,5(10)-trien-3,17β-diol 4-chloro-11β-[4-[3-(diethylamino)propyl]phenyl]-estra-1,3,5(10)-trien-3,17β-diol and 4-chloro-17α-methyl-11β-4-[3-(1-piperidinyl)propyl] phenyl]-estra-1,3,5(10)-trien-3-17β-diol.

7. A method of treating osteoporosis in warm-blooded animals comprising administering to warm-blooded animals in need thereof an amount of a compound of claim 1 sufficient to treat osteoporosis.

8. a method of treating menopausal symptoms in female warm-blooded animals comprising administering to warm-blooded animals in need thereof an amount of a compound of claim 1 sufficient to treat menopausal symptoms.

9. A method of treating menopausal symptoms in female warm-blooded animals comprising administering to female warm-blooded animals in need thereof an amount of a compound of claim 6 and its non-toxic, pharmaceutically acceptable acid addition salts.

* * * * *